(12) United States Patent
Bliss

(10) Patent No.: US 8,581,027 B2
(45) Date of Patent: Nov. 12, 2013

(54) FORWARD BREEDING

(75) Inventor: Fredrick A. Bliss, Davis, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 1039 days.

(21) Appl. No.: 12/201,221

(22) Filed: Aug. 29, 2008

(65) Prior Publication Data

US 2009/0064358 A1    Mar. 5, 2009

Related U.S. Application Data

(60) Provisional application No. 60/969,135, filed on Aug. 30, 2007.

(51) Int. Cl.
*A01H 1/04* (2006.01)
*C12N 15/10* (2006.01)

(52) U.S. Cl.
USPC ......... 800/265; 800/263; 800/264; 800/266; 800/267; 800/275; 800/300; 800/317.4; 435/6.12

(58) Field of Classification Search
None
See application file for complete search history.

(56) References Cited

U.S. PATENT DOCUMENTS

| | | | |
|---|---|---|---|
| 6,762,344 B1 | 7/2004 | Spencer et al. | 800/320.1 |
| 7,157,625 B1 | 1/2007 | Popi et al. | 800/320.1 |
| 7,176,364 B2 | 2/2007 | Weber | 800/320.1 |
| 7,189,906 B1 | 3/2007 | Tietz et al. | |
| 7,314,970 B2 | 1/2008 | Spencer et al. | 800/300 |
| 7,317,155 B1 | 1/2008 | Popi | 800/320.1 |
| 7,642,423 B2 * | 1/2010 | Nicolet et al. | 800/317.1 |
| 7,943,831 B2 * | 5/2011 | Allersma et al. | 800/317.1 |
| 2005/0144664 A1 | 6/2005 | Smith et al. | 800/267 |
| 2006/0168685 A1 | 7/2006 | Lightner et al. | 800/298 |

FOREIGN PATENT DOCUMENTS

| | | |
|---|---|---|
| EP | 1466973 A1 | 10/2004 |
| WO | WO 97/00602 | 1/1997 |

OTHER PUBLICATIONS

Quarta et al. Acta Horticulturae 465: 51-59 (1998).*
Quarta et al. Acta Horticulturae 173: 63-68 (1985).*
Sharma et al., "Genetics of resistance to bacterial wilt in tomato (Lycopersicon esculentum Mill.)," *Integrated Plant Disease Management*, 137-141, 2005.
Allard,: Principles of Plant Breeding, John Wiley & Sons, Inc., New York, 1960, (enitre book).
Bernardo, "Parental selection, number of breeding populations, and size of each population in inbred development," *Theor. Appl. Genet.*, 107:1252-1256, 2003.
Bliss, "The efficiency of developing male-sterile and male-fertile inbred components by backcrossing," *Hortscience*, 4(1):49-51, 1969.
Hallauer, "Methods used in developing maize inbreds," *Maydica*, 35:1-16, 1990.
Hartwig, "Varietal Development" In: Soybeans: Improvement, Production, and Uses, Caldwell (Ed.), Am. Soc. Agron., Madison, WI, pp. 187-210, 1973.
Heyne et al., "Wheat Breeding" In: Wheat and Wheat Improvement, Quisenberry (Ed), Am. Soc. Agron., Madison, Wi, pp. 269-306, 1967.
Isleib, "Plant genetic resources. Recovery of superior homozygous progeny from biparental crosses and backcrosses," *Crop Sci.*, 39:558-563, 1999.

* cited by examiner

*Primary Examiner* — David T Fox
(74) *Attorney, Agent, or Firm* — Dentons US LLP; Alissa Eagle Esq.

(57) ABSTRACT

A method for plant breeding comprising the steps of: selecting a donor parent possessing a trait of interest; crossing the donor parent to a first hybrid parent; selecting a first generation progeny of the cross; and crossing the first generation progeny with a second hybrid parent to produce a hybrid back cross.

25 Claims, 2 Drawing Sheets

FIG. 1

F₁ Hybrid x UP1

F₁ Hybrid x POP 1   ~t00 plants; where t = 1,...., n

POP 2 ~t00 plants; where t = 1,...., n

1) Screen Individual plants for markers/traits
2) Self plants to produce S1 families
3) Screen families for markers/traits
    a) Select .10t elite families
4) If individuals, self to produce S1 families
    .10t (*e.g*, 30) selected families
        a) Self and select to desired inbreeding to produce potential new inbreds.
        b) Cross each selected family to elite inbred to create an IBL population.
        c) Cross each selected family to Hybrid R.P.

F₁ Hybrid x

POP 3

Continue as above

FIG. 2

Scenario 1

RP      DP
CP1 x F₁CP1 x UP1)

| | Proportion | | | Percentage | |
|---|---|---|---|---|---|
| | CP1 | CP2 | UP1 | Unadapted | Commercial |
| Pop 1 | 1/2 | 0 | 1/2 | .50 | .50 |
| Pop 2 | 3/4 | 0 | 1/4 | .25 | .75 |
| Pop 3 | 7/8 | 0 | 1/8 | .13 | .87 |
| Pop 4 | 15/16 | 0 | 1/16 | .06 | .94 |

Scenario 2

RP      DP
UP1 x F₁(CP1 x CP2)

| | Proportion | | | Percentage | |
|---|---|---|---|---|---|
| | CP1 | CP2 | UP1 | Unadapted | Commercial |
| Pop 1 | 1/4 | 1/4 | 1/2 | .50 | .50 |
| Pop 2 | 1/8 | 1/8 | 3/4 | .75 | .25 |
| Pop 3 | 1/16 | 1/16 | 7/8 | .87 | .13 |
| Pop 4 | 1/32 | 1/32 | 15/16 | .94 | .06 |

Scenario 3

RP      DP
F₁(CP1 x CP2) x UP1

| | Proportion | | | Percentage | |
|---|---|---|---|---|---|
| | CP1 | CP2 | UP1 | Unadapted | Commercial |
| Pop 1 | 1/4 | 1/4 | 1/2 | .50 | .50 |
| Pop 2 | 3/8 | 3/8 | 1/4 | .25 | .75 |
| Pop 3 | 7/16 | 7/16 | 1/8 | .13 | .87 |
| Pop 4 | 15/32 | 15/32 | 1/16 | .06 | .94 |

Scenario 4

RP      DP
F₁(CP1 x UP1) x CP2

| | Proportion | | | Percentage | |
|---|---|---|---|---|---|
| | CP1 | CP2 | UP1 | Unadapted | Commercial |
| Pop 1 | 1/4 | 1/2 | 1/4 | .25 | .75 |
| Pop 2 | 3/8 | 1/4 | 3/8 | .38 | .62 |
| Pop 3 | 7/16 | 1/8 | 7/16 | .44 | .56 |
| Pop 4 | 15/32 | 1/16 | 15/32 | .47 | .53 |

FORWARD BREEDING

This application claims the priority of U.S. Provisional Application Ser. No. 60/969,135 filed Aug. 30, 2007, the entire disclosure of which is incorporated herein by reference.

BACKGROUND OF THE INVENTION

1. Field of the Invention

The present invention relates to crop breeding, and more specifically to methods for breeding new crop cultivars. The methods can be used to develop genetically-diverse selection populations by recurrent crossing of a donor line and its derivatives to one or more hybrid parents.

2. Description of Related Art

Breeders are continually developing new "line" cultivars through various plant genetic improvement programs. These cultivars are generally pureline cultivars of predominantly self-fertilized species (e.g., bean, pea, lettuce, wheat, etc.) as well as inbred line parents to produce hybrid and synthetic cultivars of both predominantly self-fertilized and cross-fertilized species (e.g., tomato, pepper, corn, sorghum, onion, carrot, etc.).

Efficient development of new line cultivars depends on combining favorable alleles for one or more important traits of interest with groups of genes that together impart outstanding field performance such as adaptation to prevailing environments, yield, and preferred horticultural and agronomic traits. Effective selection for new combinations of favorable alleles and performance traits depends on creating diverse selection populations that are segregating for genes controlling traits of interest.

Development and use of genetically-diverse selection (breeding) populations are vital to the success of a breeding program, and rightly deserves considerable attention. While investigating the optimal number and size of breeding populations for inbred line development, Bernardo (2003) made the following statement; "New inbreds are most often developed from crosses among elite inbreds in cultivar development programs (Allard 1960, p. 282). Specifically, two inbreds are first selected as parents of an F2 or backcross breeding population. New inbreds are then developed by pedigree selection, single-seed descent, or the bulk method of breeding. A breeder typically creates, selfs, and selects in several breeding populations at a time. This scheme (which has become known as advanced cycle breeding) for developing new inbreds is widely used both in self-pollinated crops such as soybean (*Glycine max* (L.) Merrill; Hartwig 1973) and wheat (*Triticum aestivum* L.; Heyne and Smith 1967), and in hybrid crops, such as maize (*Zea mays* L.; Hallauer) 1990)."

"Advanced Cycle Breeding" may be followed when the performance of an inbred parent is known and that parent is available for making new cross combinations. Other sources of useful genetic variability are elite commercial hybrids of which the parental inbreds are not commonly known or available, but which are accessible for use as a source of new gametes because they are public hybrids or registered with a Plant Variety Protection Certificate that expressly allows for such use in breeding.

When commercial $F_1$ hybrids are available, a common approach to evaluating and using them as a source of new inbred lines is to "self-down" the hybrid, select for important traits and evaluate new potential inbred parents for combining ability. This limits the genetic variability in each population to the contributions of only the inbreds that are the hybrid parents, e.g., two for a single cross, three for a 3-way, and four for a double-cross hybrid. An additional short-coming is the limited effective recombination that occurs when inbreeding is intense, i.e., with self-fertilization at each generation and even more-so when inbreds are produced from doubled haploids.

In contrast to "selfing-down", recurrent crossing to one or more hybrid (recurrent) parent(s) assures that effective recombination continues at each "backcross", whether to the same or different hybrid parent(s). The selection units chosen after each cycle of recurrent crossing can be used either for additional recurrent crossing or selected for traits of interest and performance traits including combining ability during or at the end of each generation of inbreeding.

"The potential advantage of mating genetically diverse parents is that each may contribute unique alleles, which when combined together may result in a superior individual" (Fehr, 1987). The theoretical and practical challenge is to create a selection population that has broad genetic diversity concurrent with high mean performance. Intermating parents which have one or a few elite alleles for a single trait but are otherwise less-adapted may increase the genetic diversity but also lower the mean trait phenotypic value of the selection population. On the other hand, intermating parents that are well-adapted and higher performing will likely produce a population with high mean phenotypic value, but less genetic variability. An attractive alternative approach is to use a method that allows for ongoing recombination of DNA during sexual reproduction to generate genetic variability while minimally reducing the mean trait phenotypic value of the selection population.

Typically the recurrent parent used in backcross breeding is one well-defined parent i.e., "The recurrent parent in a breeding program should be a highly acceptable genotype, except for the trait that will be altered by backcrossing. The general principle is that the genotype obtained from backcrossing will not be improved for any character except the one being transferred from the donor parent" (Fehr, 1987, p. 361).

In the standard backcross method, a recurrent parent is intended to be an inbred line that is homogeneous or nearly so rather than a hybrid. "Additionally, it should be recognized that the recurrent parent is not composed of a single pure line but is likely to be made up of many closely related pure lines" (Allard, 1960, p. 155). Further he states, "After the third backcross, however, the population usually resembles the recurrent parent so closely that selection on an individual-plant basis is largely ineffective except for the character being transferred." Clearly, when a hybrid line is used as a parent for recurrent crossing, this would not be the case.

Allard (1960, p. 151) states that, "If a backcross program is to produce a successful variety, the following three requirements must be satisfied: (1) a satisfactory recurrent parent must exist; (2) it must be possible to retain a worthwhile intensity of the character under transfer through several back-crosses; and (3) sufficient backcrosses must be used to reconstitute the recurrent parent to a high degree." Again, if a hybrid line is used as the hybrid parent during recurrent crossing, conclusions reached in (3) above would not be the case.

SUMMARY OF THE INVENTION

The present invention provides a method for plant breeding comprising, in one embodiment, the steps of: a) selecting a donor parent comprising at least a first genetic locus conferring a trait of interest; b) crossing the donor parent to a first hybrid parent; c) selecting a first generation progeny resulting from the cross in (b) that comprises the locus; and d) crossing the first generation progeny with a second hybrid parent to produce a hybrid back cross that comprises the locus. In certain embodiments, the first hybrid parent and the second hybrid parent are of the same variety. In other embodiments, the step of selecting a first generation progeny in step (c) comprises detecting the presence of the locus and/or trait of interest in the first generation progeny. In yet other embodiments, selecting a first generation progeny comprises detecting the trait of interest based on a plant phenotype.

In particular embodiments, the phenotype is resistance to a plant pathogen or plant pest, and the plant pathogen or plant pest is selected from the group consisting of a viral disease, a bacterial disease, a fungal disease, a nematode disease and an insect pest. Alternatively, in other embodiments, the phenotype is tolerance to a herbicide, including, but not limited to, glyphosate. In yet other embodiments, the phenotype is a crop quality trait. In particular embodiments, the crop quality trait is selected from the group consisting of: oil content, oil composition, protein content, protein composition, carbohydrate metabolism and fiber strength.

In other embodiments, selecting a first generation progeny comprises detecting the presence of the genetic locus, for instance wherein detecting the presence of the genetic locus comprises identifying a genetic marker linked to the locus. In particular embodiments, detecting the presence of the genetic locus comprises PCR, Southern hybridization and/or DNA sequencing.

In yet another embodiment, the method for plant breeding further comprises the step of: e) crossing a first generation progeny of the cross in (d) with a third hybrid parent to produce a first generation progeny of a subsequent generation that comprises the locus.

In further embodiments, at least two of the first hybrid parent, second hybrid parent and third hybrid parent are plants of the same variety. In other embodiments, the first hybrid parent, second hybrid parent and third hybrid parent are plants of the same variety.

The method may further comprise repeating steps d) and e) from at least 1 to 5 additional times using the progeny of a subsequent generation in step e) as the first generation progeny in step d) and using as the second hybrid parent and third hybrid parent additional hybrid plants of the same variety as the second hybrid parent and third hybrid parent, thereby producing a progeny backcrossed plant that comprises the locus.

In one embodiment, the method comprises the step of repeatedly selfing the first generation progeny of a subsequent generation a sufficient number of generations to produce an inbred line.

In other embodiments, steps d) and e) are repeated a sufficient number of generations to produce a progeny backcrossed plant that comprises the locus but otherwise comprises alleles consisting essentially of those found in the variety from which the additional hybrid plants were obtained. In other embodiments, the method comprises selecting at each generation the progeny of a subsequent generation based on the presence of the locus and/or trait of interest. In yet other embodiments the method comprises selecting at each of the generations a first generation progeny of a subsequent generation for crossing based on the presence of the locus and/or trait of interest.

In further embodiments, selecting a first generation progeny may further comprise detecting the trait of interest based on a plant phenotype. In other embodiments the phenotype is resistance to a plant pathogen or plant pest. In particular embodiments the plant pathogen or plant pest is selected from the group consisting of a viral disease, a bacterial disease, a fungal disease, a nematode disease and an insect pest. In other embodiments the phenotype is tolerance to a herbicide. In yet other embodiments the phenotype is a crop quality trait. In particular embodiments the crop quality trait is selected from the group consisting of: oil content, oil composition, protein content, protein composition, carbohydrate metabolism and fiber strength. In certain embodiments, selecting a first generation progeny comprises detecting the presence of the genetic locus. In a particular embodiment, detecting the presence of the genetic locus comprises identifying a genetic marker linked to the locus. In further embodiments, detecting the presence of the genetic locus comprises PCR, Southern hybridization and/or DNA sequencing.

By the above methods, genes and alleles controlling valuable traits can be introduced into genetically-diverse selection populations through the donor line for concurrent introgression during recurrent crossing (backcrossing). Plants resulting from recurrent crossing and gene and allele introgression can be selected for inbreeding to produce new inbred line parents with novel genotypes for use as inbred parents to create commercial cultivars in the form of $F_1$ hybrid cultivars, synthetic cultivars, and pure line cultivars.

These and other features and advantages of this invention are described in, or are apparent from, the following detailed description of various exemplary embodiments of the devices and methods according to this invention.

BRIEF DESCRIPTION OF THE DRAWINGS

Various exemplary embodiments of this invention will be described in detail, with reference to the following figures, wherein:

FIG. 1 is a diagram showing a procedure for development of selection populations using a hybrid recurrent parent.

FIG. 2 is a diagram exemplifying different scenarios for using either inbred or hybrid recurrent parents for developing selection populations.

DETAILED DESCRIPTION OF ILLUSTRATIVE EMBODIMENTS

A. Definitions

For purpose of clarity in reading the following specification and appended claims, the following terms and expressions shall have the meanings provided, wherein:

Crop Quality trait is an expression used to describe a trait related to suitability for a crop end-use, such as enhanced oil content, improved oil quality, enhanced oxidative stability of the oil, fatty acid content of the oil, fatty acid profile of the oil, protein content, specific amino acid content, milling and baking quality of a foodstuff derived from a crop, for instance a grain, forage quality, and improved fiber strength, among others.

Cultivar is a contraction of the words cultivated variety. To be classed as such, a cultivar must be distinct from other cultivars, the international equivalent of and synonym for variety (Stoskopf, 1993).

Donor parent means a plant that has a trait of interest for introgression into a cultivar. The donor parent may by homozygous (inbred), open-pollinated, or even a hybrid plant, and may be of the same or a related taxa to the hybrid parent.

Hybrid parent means a relatively heterozygous hybrid plant that may be a hybrid cultivar or a cross between two or more genetically distinct plants and possessing an array of desirable traits.

Types of cultivars (as described in Fehr, 1987, pp 377-380), include clonal cultivars, line (pure line, inbred line) cultivars, open-pollinated cultivars, synthetic cultivars, hybrid cultivars, F2 cultivars, composite cross populations, and multiline cultivars.

Line cultivars refers to a group of plants of self- or cross-pollinated species that have largely the same genetic background, defined as a theoretical coefficient of parentage of 0.87 or high higher (Kempthorne, 1987) (Fehr, 1987).

Open-pollinated refers to normally cross-pollinated plants selected to a standard that allows variation but in which the cultivars have one or more characteristics that differentiate them from other cultivars (Fehr, 1987).

Synthetic cultivars refers to progenies derived by inter-crossing a specific set of clones or seed-propagated lines. They may be either first-generation synthetics or advanced generation synthetics (Fehr, 1987).

Hybrid cultivars refers to first-generation ($F_1$) progenies from a cross produced through controlling the pollination between (a) two inbred lines, (b) two single crosses (double cross), (c) a single cross and an inbred line (three-way cross), (d) an inbred line or a single cross and an open-pollinated or a synthetic cultivar, or (e) two selected clones, seed lines, cultivars, or species (Fehr, 1987).

Selection criterion refers to the variable (trait) on which selection is based, and may be a single phenotypic measure (grain yield, protein content, growth rate, etc.) or any function of any number of phenotypic measures (Comstock, 1996).

Selection unit is the individual plant or family group among which selection is practiced (Comstock, 1996).

Response criterion refers to a phenotypic measure by which response to selection is characterized. The responses to (effects of) selection can be measured in any phenotypic trait or combination of traits, are usually of greatest concern for those coming from genotypic change in the target population. When the response criterion and the selection criterion are the same, the response to selection is called direct response, while if the selection criterion and response criterion are different, the observed change in response criterion is called correlated response (Comstock, 1996).

Selection population is the population in which selection is practiced (S-population), while genetic population refers to all the selection units that might have been produced, i.e., an infinite population of individuals or families. The genetic sample is used to designate the sample of selection units from the genetic population (the S-population) that is actually observed and from which selections are made (1996).

Target population is the population that is the prime target for improvement by the selection effort (T-population). If the main objective of the improvement program is improvement of the S-population itself, the S- and T-populations are the same. However, if for example, the aim is improvement of a population related to the S-population such as the cross between the S and some other population, that is designated the T-population (1996).

Recurrent hybrid backcross refers to a method for plant breeding where a donor parent possessing a trait of interest and a first hybrid parent are selected and crossed with the first generation offspring backcrossed to a second hybrid parent to produce a diverse selection population.

B. Examples of Advantages of the Recurrent Hybrid Backcross Method

Compared to common practice, the proposed method of recurrent hybrid backcrossing to (a) hybrid parent(s) provides a greater likelihood of obtaining new, improved inbred line parents with elite alleles introgressed from a donor parent, at a significant time saving (−15%), and less cost for trialing (i.e., Trials 3 and 4 are not needed). In both practices, it is expected that a similar amount of the elite donor parent will remain in the populations (e.g. 6.25%) and that families developed through the recurrent hybrid backcross method will be slightly more inbred.

Use of a hybrid (recurrent) parent(s) for recurrent crossing provides a dynamic population into which selected genes and alleles can be effectively and efficiently transferred and maintained using either phenotypic evaluation or linked markers for identification and selection (marker-assisted selection) during recurrent crossing. The crossing method permits the introgression of selected natural genes and alleles and constructed transgene(s) and alleles for important traits into newly-created, genetically-diverse selection populations to produce unique genetic combinations for use as inbred lines. This procedure contrasts with the current, prevailing practice of transferring natural genes and alleles and constructed transgene(s) and alleles into an existing proven inbred line employed as a recurrent parent.

The method described is ideal for creating and maintaining a genetically-diverse selection population that is a source of unique, new lines for use as commercial pure line cultivars for self-fertilizing species and inbred line parents for commercial hybrids (target populations) of either self- or cross-fertilizing plant species. This method uses recurrent crossing ("backcrossing") to a hybrid (rather than an inbred) parent that may be the same or different than the hybrid parent of the initial cross to the donor parent, has not been described previously as a method for developing unique new inbred line parents.

Recurrent crossing to one or more hybrid parents is an effective method for "forward breeding" in which the goal is to develop new inbred lines carrying one or more specified transgenes. During recurrent crossing to a hybrid recurrent parent(s), a genetically diverse population is created into which the transgene(s) is/are introgressed and maintained using molecular markers specific for the transgene(s). The resulting unique new inbred lines are potential parents for pure line cultivars or inbred parents for commercial F1 hybrids (Target Populations).

Use of this method facilitates developing unique, new inbred parents. Following each backcross this process can proceed by self- or sib-mating each individual plant with or without prior selection for one or more traits using either phenotypic (e.g., challenging with a pathogen) or genotypic (e.g., molecular marker-assisted) selection. The progeny resulting from self- or sib-pollination constitute families to which selection can be applied both among and within families by appropriate procedures. Each subsequent self- or sib-pollination results in a corresponding increase in the amount of inbreeding until potential new parents reach the desired level of inbreeding and genetic fixation.

The method has been used in advanced breeding of disease resistant lines. Bacterial wilt is a serious disease of most Solanaceous crops grown in tropical/sub-tropical regions world wide. It is soil-persistent, and difficult to avoid when land resources are scarce and long crop rotations impractical. Biological resistance to the pathogen has long been recognized as a possible means of control in tomato, but variability of the pathogen and differential effects of environmental conditions have complicated efforts to define accurate, reproducible screening procedures necessary to identify sources of resistance and incorporate resistance alleles into breeding populations and commercial cultivars.

Because of the impact of this disease, there has been extensive research and numerous sources of resistance have been identified. Most result in only low to modest levels of resistance that is variable over time and location. Although the number of resistance sources is encouraging, the complexities involved make it very difficult to pyramid resistance alleles in commercial inbred parents and resulting hybrids. With the availability of molecular markers, pyramiding becomes more achievable if the linkages between resistance alleles and polymorphic markers can be established.

C. Sources of Selected Genes and Alleles for Improving Selected Traits

There are several sources of alleles for introgression from a donor parent, e.g., simply inherited genes that display high heritability, such as dominant or recessive inheritance of disease resistance genes; quantitative trait loci (QTL) that control quantitative expression of complex traits with low to moderate (less than 1.0) heritability; and transgenes inserted into a recipient host plant by a method of genetic transformation. Alternatively, the genetic modification may be by alternative engineering techniques, such as mutation, cloning, tilling, or other methods known to the art.

Desirable qualitative traits include resistance to plant pathogens or pests, for example resistance to one or more of a viral disease, a bacterial disease, a fungal disease, a nematode disease and an insect pest. They may also be traits for increased levels of important secondary compounds, for example carotenoids that are important for human health, as well as for tolerance to a herbicide, for example, the herbicide glyphosate.

Frequency of alleles contributed by the donor parent can be maintained or increased in a diverse selection populations as a result of positive phenotypic or genotypic selection, using methods such as marker-assisted selection, observation trials, challenges with plant pathogens to ascertain level of disease resistance, etc.

Donor parents are selected on the basis of desirable qualitative or agronomic traits. In some applications the donor parent will be of the same taxa as the hybrids used for recurrent crossing, while in others the donor parent and hybrid parent will be of related taxa.

D. Development of Selection Populations

It has been a widespread practice to continue selfing the progeny of bi-parental populations for several generations to concentrate favorable alleles and increase uniformity. Isleib (1999) showed that when parents contain unequal numbers of favorable alleles, and the number of alleles by which a progeny must exceed the better parent is large, it is advantageous to backcross to the better parent prior to selfing. Backcrossing reduces the population size required to recover the favorable alleles and saves at least one generation time to reach a similar point.

When the recurrent parent is homozygous or nearly so, use of the backcross method is a conservative approach to breeding. In contrast, use of a hybrid for recurrent crossing allows for the creation of a dynamic genetically-diverse new selection population into which elite alleles for important traits can be introgressed and new unique potential parents can be derived (FIG. 1). The greatest gain from selection will occur in selection populations where there is broad genetic variability and high mean performance for important trait(s). Such populations provide a greater likelihood of producing unique inbreds with high combining ability (performance) for use in new commercial hybrids. This method of developing selection populations for "forward breeding" is not previously described. Fehr (1987, pp 136-155) devotes Chapter 12 entitled "Population Formation by Hybridization" to the subject of population development, but nowhere mentions use of hybrids as recurrent parents. He discusses use of a backcross population (p 138), but suggests using an inbred line as the recurrent parent in a conventional manner.

Using hybrid parents for recurrent crossing allows the rapid development of genetically-diverse selection populations by crossing a donor parent to a hybrid parent which is heterozygous over a wide range of the genotype, followed by recurrent crossing to the same and/or other hybrid parents. The hybrid parent may be either an existing hybrid, for instance a commercially available hybrid, or a hybrid derived by hybridizing two or more parents (i.e., single cross hybrid, 3-way hybrid, double-cross hybrid, synthetic cultivar). Genetic similarity among donor and recurrent parent(s) can be determined using pedigree analysis, molecular markers and/or hybridization schemes designed to deduce genetic relatedness.

The method allows elite genes (and alleles) from donor and hybrid parent(s) to be combined to produce unique combinations which upon inbreeding rapidly produce new inbred lines. The elite genes/alleles can be discretely defined units, i.e., qualitative genes, or, the elite genes/alleles can be those producing quantitative segregation, i.e., quantitative trait loci (QTL).

Using the method, unique genotypes are rapidly developed by recurrent crosses to one or more heterozygous hybrid parents. The unique new genotypes are also distinct from the donor parent and from the parents of that hybrid used for recurrent crossing, thus precluding the inadvertent production of new lines that could be deemed to be essentially derived from any of the parents or the hybrid(s). This is because there is no homozygous recurrent parent in the crossing scheme, and no homozygous or true-breeding line is developed until one or more generations of selfing occurs after selection in at least the first, second or third generation selection populations, ensuring the production of unique genotypes. These unique genotypes can be inbred further to produce uniform progeny for use as parents of pure-line cultivars and parents of F1 hybrid cultivars with commercial utility.

Another advantage of the method is that the unique genotypes at different stages of inbreeding can be hybridized in different combinations (testcrosses) to evaluate the potential value for use in F1 hybrid combinations.

E. Choice of Recurrent Parent

A critical decision when using a backcross-based breeding method or recurrent crossing to hybrid parents involves choice of a recurrent parent, which can be either a homozygous or near-homozygous inbred line or a hybrid parent which is genetically heterozygous. By utilizing an inbred recurrent parent the breeder insures that all gametes from the recurrent parent are essentially the same.

Choice of a hybrid (heterozygous) parent for recurrent crossing assures that with each cross a new array of recombinant gametes are transmitted to the progeny. The outcomes of using different combinations of donor and/or recurrent parent are shown in three scenarios depicted by FIG. 2. Assume for these scenarios, three inbred parents combined in different ways. There are two adapted (commercial) parents, CP1 and CP2, and one unadapted or less-adapted parent (UP 1) with some elite alleles for a trait of interest. Another option is one commercial parent and one unadapted parent.

Scenarios 1 and 2 are examples of a standard backcross procedure using a homozygous recurrent parent, where the population rapidly converges to the single genotype of the recurrent parent with increasingly less segregating gametes coming from the donor(s). In Scenario 3, the contribution of commercial parents increases at a similar rate to Scenario 1, but rather than converging on a single genotype, new recombinants are generated during meiosis at each backcross to provide a variable population with predominantly commercial phenotypes. When the donor parent is an unadapted line, the contribution from that parent diminishes rapidly with each backcross, providing limited opportunity for recombination among commercial and unadapted genes. In some cases that may be desirable to reduce genetic drag (linkage of deleterious genes with useful genes being selected).

A hybrid parent for recurrent crossing will be chosen based on outstanding performance. More specifically, it will be one with not only high $F_1$ performance but also a high mean performance of F2 individuals and fixed lines derived from inbreeding to near homozygosity, that perform well either as pure line cultivars (self-pollinating crop) or as inbred parents for commercial $F_1$ hybrids (self- or cross-pollinating crops).

After deciding to use a hybrid (heterozygous) parent for recurrent crossing, one of several options can be chosen. In Scenario 3, a hybrid between two commercial parents is used, e.g., a currently existing commercial $F_1$ hybrid or a new cross between two well adapted inbred parents that between them possess complementary traits.

However, to provide greater opportunity for recombination among adapted and unadapted genes, the three lines can be crossed and backcrossed as in Scenario 4. A hybrid between a commercial parent and a less-adapted parent that contains elite genes for one or a few traits is used as the recurrent parent. To initiate the process, another commercial inbred is included to provide a greater proportion of "commercial" genes in the initial selection population, thereby raising the expected population mean value and increasing the likelihood of obtaining progeny that outperform the best parent contributing to the population. If the two commercial parents are unequal in performance, the better one should be the hybrid recurrent parent. If CP2 was superior to CP1, changing places of the two commercial parents would be warranted. Both the percentage unadapted and percentage commercial converge on 0.50 at a diminishing rate, with the contribution to the commercial component from CP1 increasing and from CP2 decreasing.

In both Scenarios 3 and 4, individuals in Pops 2-4 would be more genetically diverse than those in Scenarios 1 and 2, due to the use of heterozygous recurrent parents.

When backcrossing to a heterozygous recurrent parent as in Scenarios 3 and 4, inbreeding will result in the progeny populations but at a slower rate than when an inbred parent is used as the recurrent parent (Bliss, 1969). To reduce the rate of inbreeding to zero (or negligible levels), an unrelated hybrid can be used for each backcross.

It is highly unlikely that genotypes identical to the parents of a hybrid used as the recurrent parent will be recovered, but rather new combinations of genes coming from the original parents would occur at frequencies sufficient for identification of potential elite inbred line parents using phenotypic selection, progeny tests, combining ability, etc. The recombination of genes from the hybrid parent(s) used for recurrent crossing in combination with elite alleles from the donor parent represent unique, new combinations that have utility for commercial application.

F. Detection of Quality and Other Traits

Where the trait of interest is a plant phenotype, selection for the trait may be by any of the ways known to the art, for example detecting or quantifying an expressed trait (selection criterion). In some cases the trait of interest may be easily monitored by the presence or absence of a marker sequence known to be linked to the gene(s) controlling the trait of interest. This will be true in those cases where the trait has been introduced by a genetic modification to the donor parent. In other instances the trait may be readily detected based on the phenotype. Any similar or other process for detecting the trait may therefore be used, as is known in the art.

Example 1

Developing Unique Inbred Lines

A common goal of crop breeding is to develop new inbred line parents (families) that can be used; 1) as inbred parents to create commercial $F_1$ hybrid cultivars (e.g., maize, sorghum, tomato, pepper, etc.), and/or 2) as a single inbred parent to create a commercial pure line cultivar (e.g., soybean, common bean, lettuce, garden pea, etc.). New inbred families can result from gene recombination that occurs in segregating populations derived from hybridization of genetically-different parents, followed by inbreeding through inter-mating siblings and/or self-fertilization of progeny resulting from the hybridization.

To initiate the process, two lines are intercrossed (P1×P2) to create a hybrid population of one or more plants each of which is heterozygous at loci for which the parents differ. The hybrid population (Hybr) can arise in several ways among which are; 1) parents that show complementary traits are hybridized, the assumption being that for the complementary traits, controlling loci will be heterozygous, 2) a commercially-successful hybrid is identified, the assumption being that success in the market place is due to the presence of elite alleles coming from one or both original parents and the hybrid is heterozygous at loci for which the parents differ.

It is common practice to "self-down" one or more plants of the hybrid population for several generations to produce a selection population of new inbred lines with a specified amount of homozygosity due to inbreeding (Table 1).

TABLE 1

Developing new inbred families by "self-down" of a hybrid parent followed by introgression of elite alleles from a donor parent by backcrossing.

| Generation | % elite donor parent | Inbreeding (per locus basis) | |
|---|---|---|---|
| Parental (P1 &P2) | 0 | 1.00 | |
| P1 × P2 = Hybrid | 0 | 0 | |
| Hybr × self = S1 | 0 | 0.50 | |
| S1(x) = S2 | 0 | 0.75 | |
| S2(x) = S3 | 0 | 0.875 | |
| Trial - 1 | | | Select best S3 |
| Trial - 2 | | | families for allele introgression |
| S4 × Donor = F1 | 50% | 0 | |
| S4 × F1 = BC1 | 25 | 0.50 | |
| S4 × BC1 = BC2 | 12.5 | 0.75 | |
| S4 × BC2 = BC3 | 6.25 | 0.875 | |
| Trial - 3 | | | Select best BC3 |
| Trial - 4 | | | inbred families with elite allele |

When the level of inbreeding defined for new line cultivars is reached (i.e., 0.875) (Fehr, 1987), new inbred lines (i.e., S3 families) can be grown in trials (1 and 2) to identify the ones with commercial potential for new hybrid parents or pureline parents.

The common practice is to use the inbred families (e.g., S3) selected from trials 1 and 2, to introgress one or more elite alleles from a donor parent (DP) by crossing to one or more selected S3 families, followed by three or more backcrosses to each S3 line, each of which becomes a recurrent parent (RP). In addition to producing putative new inbred lines from a hybrid parent by "selfing down", another action may be to introgress (introduce) into the new lines valuable, elite alleles not found in either parent of the hybrid which is the source of the new putative inbreds. When the common practices of "selfing down" and allele introgression are done in tandem, five generations (parental through S3) are needed for the self-down phase, two generations of trials are needed to select the best S3 families, four (4) generations of crossing and backcrossing to each selected S3 family is needed and at least two more generations of trials are required to complete the procedure, for a total of thirteen (13) generations.

In contrast to the common practice requiring thirteen (13) generations to produce putative new inbred lines containing an elite introgressed allele, a scheme was developed in which similar end products, i.e., putative new inbred lines containing the elite allele, can be developed by crossing the source of the allele (donor parent (DP)) to the hybrid parent, followed by recurrent backcrosses to the hybrid parent (Table 2).

TABLE 2

Developing new inbred families by concurrent introgression of elite alleles from a donor parent while backcrossing to a hybrid parent.

| Generation | % elite donor parent | Inbreeding (per locus basis) | |
|---|---|---|---|
| Parental (P1&P2) | 0 | 1.00 | |
| P1 × P2 = Hybrid | 0 | 0 | |
| Hybr × Donor = F1 | 50% | 0 | |
| Hybr × F1 = BC1 | 25 | 0.25 | |
| Hybr × BC1 = BC2 | 12.5 | 0.2795 | |
| Hybr × BC2 = BC3 | 6.25 | 0.2825 | |
| BC4 × self = S1 | 6.25 | 0.283 + 0.359 = 0.64 | |
| S1(x) = S2 | 6.25 | 0.82 | |
| S2(x) = S3 | 6.25 | 0.91 | |
| Trial - 1 | | | Select best S3 |
| Trial - 2 | | | inbred families with elite allele |

The recurrent hybrid backcross method (Table 2) provided a savings of two generations of trialing (2/13=15% time reduction), with a higher level of inbreeding at a comparable stage (i.e., 6.25% of elite donor parent in S3 or BC3 families to be selected). This small increase in inbreeding is noteworthy because it is important to have true breeding inbred lines for parents of commercial $F_1$ hybrids.

The method of recurrent crossing to hybrid parents differs from the standard practices in other ways. In the standard practice, inbreeding during "self-down" proceeds very quickly thereby limiting the opportunity for recombination and appearance of new, potentially valuable new gene combinations. In the recurrent hybrid method the level of inbreeding proceeds slowly during the introgression of the elite allele during backcrossing to the genetically-heterozygous, hybrid (Hybr) parent. This slow rate of inbreeding favors effective genetic recombination and increases the likelihood of favorable new gene combinations that can be identified during trialing (Trials 1 and 2) (Table 2) to be used as true breeding inbred lines for parents of commercial F1 hybrids.

In the recurrent hybrid backcross method, the elite donor parent is crossed to the hybrid in the $3^{rd}$ generation; therefore genetic material from the donor, including the elite alleles of interest, are contributing to opportunities for recombination that can provide improved inbred families. In contrast, in the standard practice the elite donor parent is first crossed to selected S3 families in generation nine. Contribution from the donor parent cannot be utilized before that time and will not be included in earlier recombination such as occurs in the recurrent hybrid backcross method.

Although the foregoing invention has been described in some detail by way of illustration and example for purposes of clarity and understanding, it will be obvious that certain changes and modifications may be practiced within the scope of the invention, as limited only by the scope of the appended claims.

Example 2

Development of Bacterial Wilt Resistant Tomato Inbreds Using Recurrent Backcrossing to Hybrid Parents Pollen from a tomato donor parent known to have field resistance to bacterial wilt disease but having commercially unacceptable fruit and plant characteristics, was transferred to the stigmas of plants of a commercially-available tomato hybrid cultivar (hybrid 1) having intermediate field resistance ("IR") and good quality fruit and plant characteristics, in order to produce seeds (offspring 1).

Pollen was collected in bulk from plants of offspring 1 and transferred to the stigmas of hybrid 1, four other commercially-available hybrid cultivars (hybrids 2, 3, 4, 5) with minimal or intermediate field resistance, and three hybrids (hybrids 6, 7, 8) each the result of hybridizing two parents with field resistance ("R") or intermediate field resistance to bacterial wilt (caused by *Ralstonia solanacearum* (Smith 1896) Yabuuchi et al. 1996). Pollen was collected from 15-20 plants of offspring 1 and constituted a bulk sample with which to pollinate hybrids 1 through 8, i.e., recurrent backcrossing to hybrids. Two fruits which contained seeds resulting from bulk pollinations to each of the eight hybrid parents were collected from each hybrid parent (offspring 2-9).

About 100 seeds from each of offspring 2-9 were sown, and approximately 750 resulting seedlings were screened with molecular markers diagnostic for levels of resistance to bacterial wilt disease. Approximately ⅔ of the seedlings were discarded as undesirably susceptible to the bacterial wilt disease. Of the approximately ⅓ or 250 saved seedlings, each was self fertilized to produce seeds, resulting in ~250 S1 families.

Seeds of the ~250 S1 families were sown to produce plants which were grown in trials in Asia and North America. The trials were conducted in fields known to contain the bacterial wilt disease pathogen. Plants of each S1 family were grown in replicated plots assigned randomly to the field to assure accurate and valid estimates of the level of resistance or susceptibility to the bacterial wilt disease. The level of resistance to bacterial wilt of each S1 family was estimated from the number of wilted (dead) plants in each of the replicated plots. Included with the S1 families were replicated plantings of standard tomato entries known to be either susceptible ("S"; i.e. ~ all to 29% plants wilted), intermediately resistant (IR; ~30 to 70% of plants wilted), or resistant (R; ~ none to 31% plants wilted) to bacterial wilt.

The ~250 S1 families were each tested for one season at two sites in Asia and one site in North America. At each site, families were identified with higher levels of resistance to *R. solanacearum* than the resistant donor parent and the hybrids used for recurrent backcrossing, each of which having been designated as S, IR, or R to bacterial wilt. Individual plants showing no wilting symptoms and with good fruit and plant characteristics were identified in the families with consistently high levels of resistance to the wilt disease and seeds were saved from fruits of those selected plants.

Seeds from each of the selected fruit were referred to as S2 families. Plants of these S2 families were grown another year at two sites in Asia in a similar manner to that described for the S1 families. At each site, families were identified with higher levels of resistance to the bacterial wilt disease than the resistant donor parent and the hybrids used for recurrent backcrossing, each of which having been designated as S, IR, or R to bacterial wilt. Each family was evaluated for fruit and plant characteristics. Plants with the best combination of resistance to bacterial wilt, and fruit and plant traits were saved as potential new inbred parents.

REFERENCES

The following references, to the extent that they provide exemplary procedural or other details supplementary to those set forth herein, are specifically incorporated herein by reference:

Allard, R. W. 1960. Principles of Plant Breeding. John Wiley & Sons, Inc. New York.
Bernardo, R. 2003. Parental selection, number of breeding populations, and size of each population in inbred development. *Theor. Appl. Genet.* 107:1252-1256.
Bliss. F. A. 1969. The Efficiency of Developing Male-sterile and Male-fertile Inbred Components by Backcrossing. *HortScience* 4(1):49-51.
Comstock, R. E. 1996. Quantitative Genetics with Special Reference to Plant and Animal Breeding. Iowa State Univ. Press, Ames.
Fehr W. R. 1987. Principles of Cultivar Development. Vol. 1. MacMillan Publ. Co., Inc. New York.
Hallauer, A. R. 1990. Methods used in developing maize inbreds. *Maydica* 35:1-16.
Hartwig, E. E. 1973. Varietal development. In: B. E. Caldwell (ed) Soybeans: Improvement, Production, and Uses. Am. Soc. Agron., Madison, Wis., pp 187-210.
Heyne, E. G., and G. S. Smith. 1967. Wheat breeding. In: K. S. Quisenberry (ed) Wheat and Wheat Improvement. Am. Soc. Agron., Madison, Wis., pp 269-306.
Isleib, T. G. 1999. Recovery of superior homozygous progeny from biparental crosses and backcrosses. *Crop Sci.* 39:558-563.
Kempthorne, 0. 1957. An Introduction to Genetic Statistics. John Wiley, New York.

What is claimed is:

1. A method for plant breeding comprising the steps of:
a) selecting a donor parent comprising at least a first genetic locus conferring a trait of interest;
b) crossing the donor parent to a first hybrid parent, said first hybrid parent defined as being derived from a cross of two inbred varieties;
c) selecting a first generation progeny resulting from the cross in (b) that comprises the locus;
d) crossing the first generation progeny with a second hybrid parent of the same variety as said first hybrid parent to produce a hybrid backcross that comprises the locus; and
e) crossing the hybrid backcross of (d) with a third hybrid parent to produce a subsequent generation progeny that comprises the locus;
wherein the third hybrid parent is of the same variety as the first hybrid parent and wherein the first hybrid parent is of a species selected from the group consisting of bean, pea, lettuce, wheat, tomato, corn, sorghum, onion, and carrot.

2. The method of claim 1, wherein selecting a first generation progeny in step (c) comprises detecting the presence of the locus and/or trait of interest in the first generation progeny.

3. The method of claim 2, wherein selecting a first generation progeny comprises detecting the trait of interest based on a plant phenotype.

4. The method of claim 3, wherein the phenotype is resistance to a plant pathogen or plant pest.

5. The method of claim 4, wherein the plant pathogen or plant pest is selected from the group consisting of a viral disease, a bacterial disease, a fungal disease, a nematode disease and an insect pest.

6. The method of claim 3, wherein the phenotype is tolerance to a herbicide.

7. The method of claim 3, wherein the phenotype is a crop quality trait.

8. The method of claim 7, wherein the crop quality trait selected from the group consisting of: oil content, oil composition, protein content, protein composition, carbohydrate metabolism and fiber strength.

9. The method of claim 2, wherein selecting a first generation progeny comprises detecting the presence of the genetic locus.

10. The method of claim 9, wherein detecting the presence of the genetic locus comprises identifying a genetic marker linked to the locus.

11. The method of claim 9, wherein detecting the presence of the genetic locus comprises PCR, Southern hybridization and/or DNA sequencing.

12. The method of claim 1, further comprising repeating steps d) and e) from at least 1 to 5 additional times using the subsequent generation progeny in step e) as the first generation progeny in step d) and using as the second hybrid parent and third hybrid parent additional hybrid plants of the same variety as the second hybrid parent and third hybrid parent, thereby producing a progeny backcrossed plant that comprises the locus.

13. The method of claim 12, wherein steps d) and e) are repeated a sufficient number of generations to produce a progeny backcrossed plant that comprises the locus but otherwise comprises alleles consisting essentially of those found in the variety from which the additional hybrid plants were obtained.

14. The method of claim 1, comprising the step of repeatedly selfing the subsequent generation progeny a sufficient number of generations to produce an inbred line.

15. The method of claim 12, comprising selecting at each generation the subsequent generation progeny based on the presence of the locus and/or trait of interest.

16. The method of claim 13, comprising selecting at each of the generations a subsequent generation progeny for crossing based on the presence of the locus and/or trait of interest.

17. The method of claim 16, wherein selecting a subsequent generation progeny comprises detecting the trait of interest based on a plant phenotype.

18. The method of claim 17, wherein the phenotype is resistance to a plant pathogen or plant pest.

19. The method of claim 18, wherein the plant pathogen or plant pest is selected from the group consisting of: a viral disease, a bacterial disease, a fungal disease, a nematode disease and an insect pest.

20. The method of claim 17, wherein the phenotype is tolerance to a herbicide.

21. The method of claim 17, wherein the phenotype is a crop quality trait.

22. The method of claim 21, wherein the crop quality trait selected from the group consisting of: oil content, oil composition, protein content, protein composition, carbohydrate metabolism and fiber strength.

23. The method of claim 16, wherein selecting a subsequent generation progeny comprises detecting the presence of the genetic locus.

24. The method of claim 23, wherein detecting the presence of the genetic locus comprises identifying a genetic marker linked to the locus.

25. The method of claim 23, wherein detecting the presence of the genetic locus comprises PCR, Southern Hybridization and/or DNA sequencing.

\* \* \* \* \*